United States Patent [19]

Shah et al.

[11] Patent Number: 4,775,456

[45] Date of Patent: Oct. 4, 1988

[54] ELECTROCHEMICAL GAS SENSOR

[75] Inventors: Atul S. Shah; Jay M. Lauer, both of Hacienda Heights; Carl R. Jones, San Gabriel, all of Calif.

[73] Assignee: Teledyne Industries, Inc., Los Angeles, Calif.

[21] Appl. No.: 10,266

[22] Filed: Feb. 2, 1987

[51] Int. Cl.[4] .......................................... G01N 27/46
[52] U.S. Cl. ...................................... 204/412; 204/415
[58] Field of Search ........................ 204/1 P, 415, 412

[56] References Cited

U.S. PATENT DOCUMENTS

| | | | |
|---|---|---|---|
| 3,272,725 | 9/1966 | Garst | 204/415 |
| 3,328,277 | 6/1967 | Solomons et al. | 204/195 |
| 3,429,796 | 2/1969 | Lauer | 204/195 |
| 3,454,485 | 7/1969 | Hauk et al. | 204/195 |
| 3,526,577 | 9/1970 | Molloy | 204/1 P |
| 3,539,455 | 11/1970 | Clark | 204/1 |
| 3,668,101 | 6/1972 | Bergman | 204/195 |
| 3,707,455 | 12/1972 | Derr et al. | 204/415 |
| 3,767,552 | 10/1973 | Lauer | 204/195 |
| 3,855,096 | 12/1974 | Bergman | 204/1 P |
| 4,152,233 | 5/1979 | Chand | 204/195 |
| 4,435,268 | 3/1984 | Martin et al. | 204/408 |

Primary Examiner—T. Tung
Attorney, Agent, or Firm—Ronald W. Reagin; Stephen L. King

[57] ABSTRACT

An electrochemical gas analyzer is disclosed which includes sensing, compensation and counter electrodes in an electrolyte. The compensation electrode provides a compensation signal related to the concentration of gas dissolved in the bulk of the electrolyte. This compensation signal is subtracted from the analyzer output signal to eliminate errors caused by bulk electrolyte dissolved gas.

5 Claims, 3 Drawing Sheets

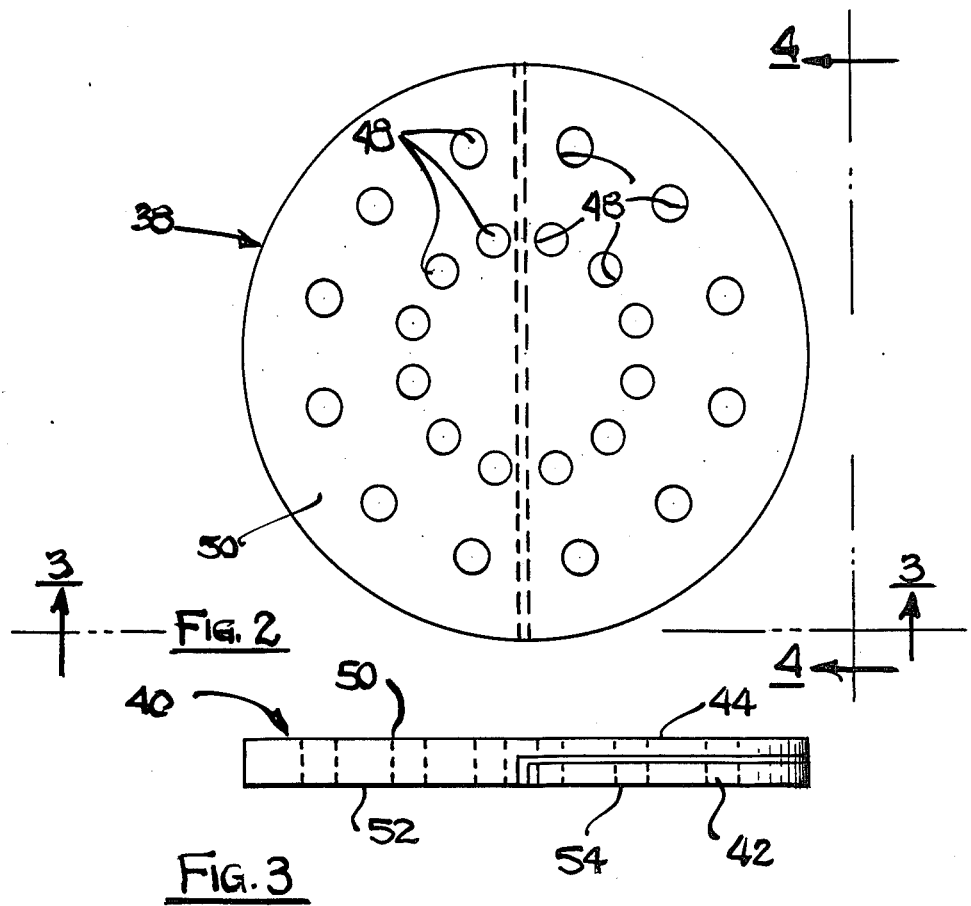
Fig. 2
Fig. 3
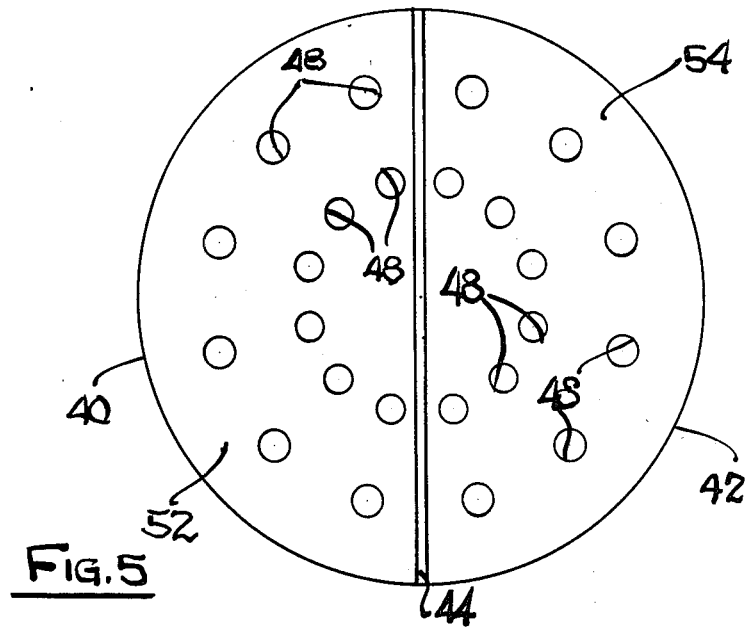
Fig. 5

ELECTROCHEMICAL GAS SENSOR

BACKGROUND OF THE INVENTION

This invention relates to electrochemical gas sensors and, more particularly, to an electrochemical gas sensor which is substantially more accurate than prior art sensors.

A wide variety of electrochemical gas sensors have been designed over the years to measure the concentration, or partial pressure, of a particular gas in a mixture of gases. One application for such a sensor is to provide an indication of the concentration of oxygen in gaseous mixtures.

One class of such sensors includes a sensing electrode, a counter-electrode, an electrolyte in contact with both electrodes, a membrane adjacent a surface of the sensing electrode, and a path for the gas to be measured to dissolve into and diffuse through the electrolyte. When the dissolved gas diffuses through the electrolyte and contacts the sensing electrode, a measurable current can be detected in an external circuit connected between the electrodes. In a galvanic type sensor, the measurable current flows without application of an external voltage, while a polarographic type sensor requires the application of an external voltage in order to produce the measurable current. The present invention is applicable to both types of sensors. Examples of sensors of the type described above are disclosed in U.S. Pat. Nos. 3,429,796, issued Feb. 25, 1969; and 3,767,552, issued Oct. 23, 1973, both assigned to the assignee of the present invention.

An important consideration in the design of a gas sensor is that the output signal derived from the cell be proportional to the partial pressure of the measured gas in the gas mixture. However, in most of the prior art sensors, the output signal is not only responsive to the incoming gas concentration, but is also responsive to the gas previously dissolved in the bulk of the electrolyte distributed between the electrodes. This dissolved gas is generally the result of previous exposure of the sensor to a high concentration of the gas. Because the output signal provided by prior art sensors includes a component related to previously dissolved gas in the electrolyte, the accuracy of these sensors is a function of the gas exposure history of the sensor. This accuracy limitation severely limits the application of these prior art sensors in the detection of low concentrations of gas.

Several attempts have been made to eliminate the sensor errors caused by gas dissolved in the bulk of the electrolyte. One method employs the addition of a scavenger electrode positioned in the bulk of the electrolyte. The scavenger electrode is connected to an electrical circuit so that it acts in essence as a second sensing electrode.

The object of the scavenger electrode is to reduce (or oxidize) the gas in contact with it before that gas diffuses through the bulk electrolyte to the sensing electrode, thus eliminating sensing error. In order for the scavenger electrode to be effective, it must prevent any of the dissolved gas from diffusing back to the sensing electrode. Unfortunately, the electrochemical reaction which consumes the dissolved gas can only occur at the surface of the scavenger electrode. Thus, the scavenger does not have an effect on gas which diffuses through or around it. Accordingly, the scavenger electrode mechanizations do not eliminate the sensing errors to the degree necessary for accurately measuring extremely low concentrations of gas. An example of the scavenger electrode mechanization described above is disclosed in U.S. Pat. No. 3,454,485, issued July 8, 1969 to P. Hauk, et al.

Accordingly, it is an object of the present invention to provide a new and improved electrochemical gas analyzer.

It is another object of the present invention to provide an electrochemical gas analyzer capable of providing an output signal which is not responsive to gas previously dissolved in the analyzer electrolyte.

It is yet another object of the invention to provide a gas analyzer having a compensation electrode which produces a signal related to the gas previously dissolved in the electrolyte.

SUMMARY OF THE INVENTION

The foregoing and other objects of the invention are accomplished by providing an electrochemical gas analyzer for measuring the concentration of a gas in a gas mixture. The analyzer includes a counter-electrode mounted in a housing which supports a membrane permeable to the gas.

A sensing electrode is also mounted within the housing and has first and second surfaces. The first surface is adjacent the permeable membrane, and the second surface is further away from the permeable membrane than the first surface.

A liquid electrolyte is contained within the housing and is in contact with the counter electrode, the first surface of the sensing electrode, and a portion of the second surface of the sensing electrode. The gas to be measured passes through the permeable membrane and dissolves into the electrolyte.

An electrical insulator is provided which is impermeable to the gas and liquid and has first and second opposing surfaces. The first insulator surface covers substantially all but the first portion of the second surface of the sensing electrode, whereby the gas dissolved in the electrolyte cannot contact the covered surface.

A compensating electrode is also provided which covers a predetermined area of the second insulator surface and is in contact with the electrolyte.

The sensing and counter electrodes are connected to an electrical circuit to provide a first signal which is related to the concentration of gas dissolved in the electrolyte which contacts the surfaces of the sensing electrode.

The compensating and counter electrodes are connected to a second electrical circuit to provide a second signal which is related to the concentration of the gas dissolved in the bulk of the electrolyte which contacts the second surface of the sensing electrode.

The second signal is subtracted from the first signal to provide an output signal which is related to substantially only the concentration of gas dissolved in the thin film of electrolyte which contacts the first surface of the sensing electrode.

Other objects, features and advantages of the invention will become apparent from a reading of the specification taken in conjunction with the drawings in which like reference numerals refer to like elements throughout the several figures.

BRIEF DESCRIPTION OF THE DRAWINGS

FIG. 2 is a top view of the sensor and compensation electrode assembly employed in the analyzer of FIG. 1;

FIG. 3 is a front view of the assembly of FIG. 2;

FIG. 5 is a bottom view of the assembly of FIG. 2;

DESCRIPTION OF THE PREFERRED EMBODIMENT

Figure 1:
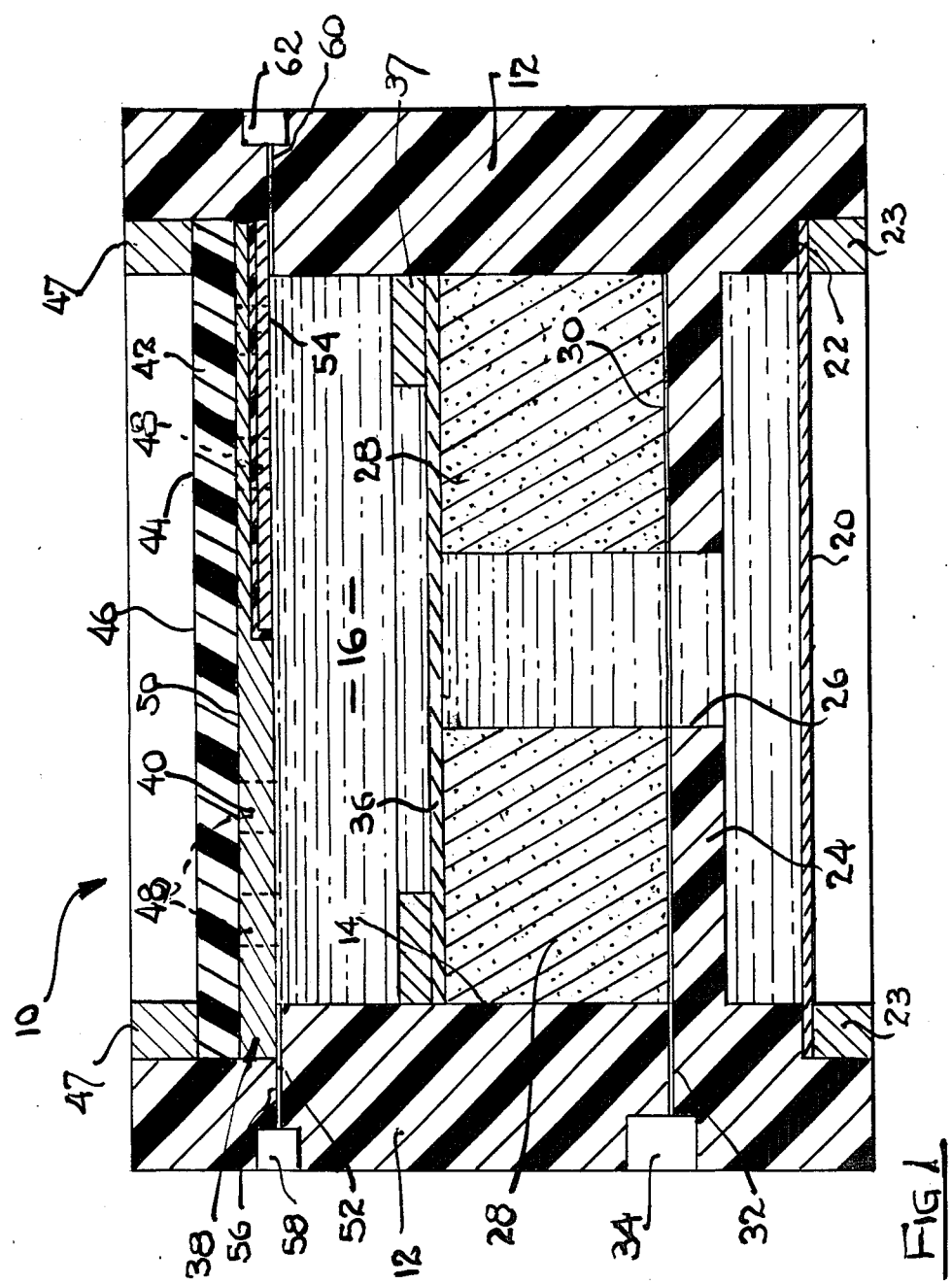
FIG. 1 is a cross-sectional view of a gas analyzer constructed in accordance with the invention.
Figure 4:
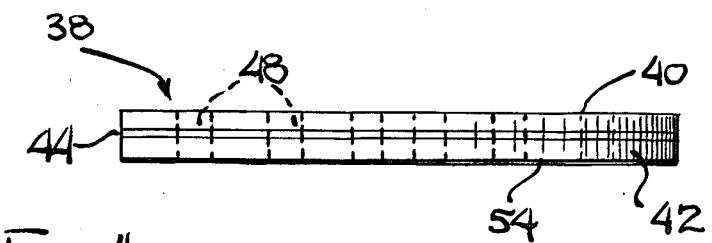
FIG. 4 is a side view of the assembly of FIG. 2.

FIG. 1 is a cross-sectional view of a galvanic type electrochemical oxygen analyzer 10 constructed in accordance with the teachings of the invention. A generally cylindrical housing 12 is provided which is formed of a plastic material such as polyethylene. An axial passage 14 extends through the housing 12 and forms an electrolyte chamber 16 which is closed at the bottom by a flexible expansion membrane 20 attached to a shoulder 22 of the housing 12, and held in place by a ring 23.

A flange 24 having a central aperture 26 is provided above the shoulder 22 to support a counter-electrode in the form of an anode 28. The anode 28 is formed of a porous non-polarizable metal such as sintered lead which is pressed into a generally toroidal shape. An anode contact plate 30 is provided to ensure good electrical contact to the anode 28. A wire 32 is welded to the plate 30 and threaded through an opening in the housing 12 to an anode contact 34. The top surface of the anode 28 is covered by a liquid permeable disc 36 held in place by ring 37. The disc 36 is formed of filter paper or the like to contain loose particles from the anode 28.

The chamber 16 is covered at the top by an electrode assembly 38 which includes a sensing electrode in the form of a cathode 40 to which is attached a compensating electrode 42. The electrode 42 is electrically isolated from the cathode 40 by means of a liquid and gas impermeable insulator 44.

The cathode 40 and compensating electrode 42 may be formed of a noble metal such as gold, silver or platinum, or may be a base metal such as brass, which is plated with a noble metal. A wire 56 is attached to the cathode 40 and passes through an opening in the housing 12 to an external cathode contact 58. In similar fashion, a wire 60 is attached to the compensating electrode and passes through an opeing in the housing 12 to an external contact 62.

A gas-permeable, liquid-impermeable membrane 46 formed of a material such as Teflon covers a first surface 50 of the cathode 40 to form a liquid tight enclosure for the chamber 16, and is held in place using a ring 47. The chamber 16 is filled with a liquid electrolyte such as a ten percent solution of potassium hydroxide which contacts a first portion 52 of a second surface of the cathode 40, the second surface 54 of the compensating electrode 42, and the anode 28. The assembly 38 includes a plurality of apertures 48 which provide a path for the electrolyte to wet the top surface 50 of the cathode 40 adjacent the membrane 46. These apertures 48 need not be provided in the assembly 38, but may, for example, be provided in the housing 12 surrounding the assembly 38 to enable electrolyte to reach the surface 50 of the cathode 40.

The operation of the analyzer 10 described thus far is as follows. The gas to be measured (oxygen, in this instance), which is usually one component in a gas mixture, enters the analyzer by passing through the permeable membrane 46. The gas dissolves into the thin layer of electrolyte between the membrane 46 and the first surface 50 of the cathode 40. A portion of the incoming dissolved gas, by diffusion, migrates through the apertures 48 into the bulk of the electrolyte in the chamber 16, where it remains trapped until it can diffuse back to the electrode assembly 38.

When an external current path is established between the contacts 58 and 34, a measurable current will flow between the cathode and anode which is related to the concentration of the gas dissolved in the electrolyte which contacts the surfaces 50 and 52 of the cathode 40. The current produced in response to the concentration of gas which contacts the surface 50 of the cathode 40 is an accurate measure of the oxygen concentration in the incoming gas mixture. However, the current produced in response to the concentration of gas which contacts the surface 52 of the cathode 40 is a measure of the concentration of oxygen dissolved in the bulk electrolyte in the chamber 16, usually as a result of a prior exposure of the analyzer to a high concentration of oxygen.

The external current signal provided by the analyzer 10 is thus proportional to the sum of the desired incoming gas concentration and the undesired bulk electrolyte dissolved gas concentration. Accordingly, the analyzer signal includes an error which is related to the exposure history of the analyzer. Such an error makes it extremely difficult to obtain accurate readings of low gas concentrations.

The analyzer 10 of the present invention includes a compensating electrode 42 for compensating the analyzer current output signal to eliminate the error caused by the gas dissolved in the bulk electrolyte. Referring to FIGS. 2-6 there are shown detail views of the assembly 38, which includes the compensating electrode 42. One way of constructing the assembly 38 (see FIG. 6) is to form the cathode 40 as a solid metal disk. A portion of the second surface is cut away to form a first portion 52 of the second surface, and a second portion 53 of the second surface in a generally semi-circular recess. A layer of insulator 44, which may be epoxy resin or the like, and having first and second opposing surfaces 57 and 59, is placed within the recess to form an electrically isolated cavity. The surface 57 covers the surface 53 and prevents electrolyte and gas from contacting the surface 53. A first surface 55 of the compensation electrode 42 is adhesively attached to the surface 59 of the insulator 44, whereby the second surface 54 of the electrode 42 is coplanar with the first portion of the second surface 52 of the cathode 40. Preferably, the area of the surface 54 is made substantially identical to the area of the surface 52.

An alternate way of constructing the assembly 38 is to start with an insulator in the form of a solid disk having the outside dimensions of the assembly 38. The disk may be formed of an inert, non-permeable plastic such as ABS, glass filled epoxy, or the like. The disk is then covered with a suitable metal on all surfaces, including the edge, in all areas except the insulated areas 44 shown by the bold lines in FIGS. 3, 4 and 5. The disk may be covered by metal using plating, laminating, silk screening, vacuum deposition or other methods well known in the art. The result is the formation of the cathode 40 and the compensation electrode 42 having the shape and dimensions as described above. In either method of construction, apertures 48 are provided in the assembly 38 to permit flow through of the electrolyte.

The operation of the compensating electrode 42 is as follows. Referring to FIG. 1, it may be seen that gas trapped in the bulk electrolyte in the chamber 16 causes the analyzer current error signal by diffusing through the electrolyte into contact with the bottom surface 52 of the cathode 40. Because the surface 54 of the electrode 42 is substantially coplanar with the surface 52, a similar concentration of gas will diffuse from the bulk electrolyte to the surface 54 as to the surface 52.

Accordingly, when an external compensation current path is established between the contacts 62 and 34, a measurable current will flow between the compensating electrode 42 and the anode 28. This current is related to the concentration of the gas dissolved in the bulk electrolyte which has diffused into contact with the surface 52 of the cathode 40. Thus, the compensating current represents the error produced in the analyzer current signal due to bulk electrolyte dissolved gas. By subtracting the compensation current from the analyzer current, an output signal may be realized which is free from the error produced by the bulk electrolyte dissolved gas.

Figure 7:
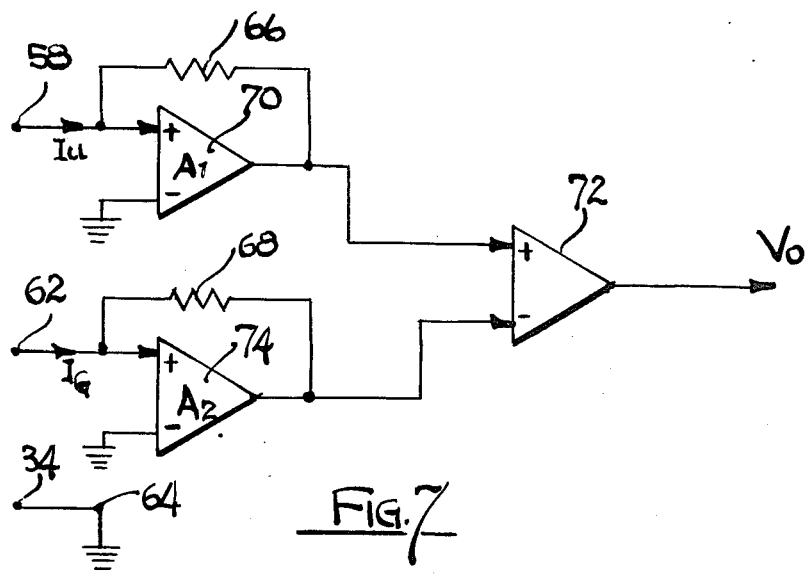
FIG. 7 is a schematic/block diagram of circuitry used to process signals from the analyzer of FIG. 1 to provide a compensated gas concentration output signal.

FIG. 7 shows a schematic/block diagram of a circuit which may be used to process the signals from the analyzer 10 to provide a substantially error free output signal. The anode contact 34 is connected to a signal ground terminal 64. The cathode contact 58 is connected to a negative input terminal of a current to voltage amplifier 70 having a gain $A_1$, set by resistor 66. The positive input terminal of amplifier 70 is grounded. The amplifier 70 acts to amplify the cathode current $I_u$ representing the uncompensated analyzer signal. The output signal from the amplifier 70 is provided to a positive input terminal of a differential amplifier 72.

The compensating electrode contact 62 is connected to a negative terminal of a current to voltage amplifier 74 having a gain $A_2$ set by resistor 68. The positive input terminal of amplifier 74 is grounded, and the output terminal is connected to the negative input terminal of the amplifier 72. The amplifier 74 acts to amplify the compensation electrode current $I_c$ representing the analyzer compensation signal.

Figure 6:
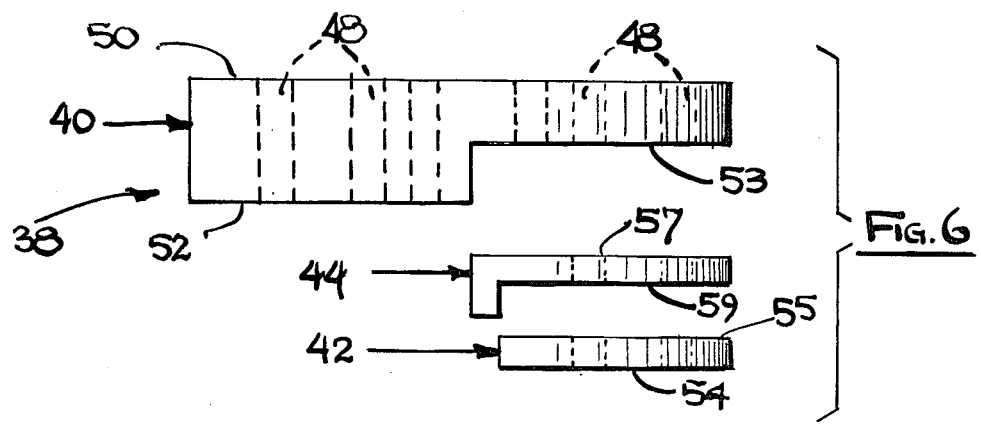
FIG. 6 is an exploded front view of the assembly of FIG. 2.

The operation of the circuitry shown in FIG. 6 is as follows. The signal $V_o$ appearing at the output terminal of the differential amplifier 72 is the difference between the signals $A_1 \cdot I_u$ and $A_2 \cdot I_c$. It may be shown that compensation of the signal $I_u$ to account for the bulk electrolyte dissolved gas in the analyzer 10 to produce a substantially error-free output signal $V_o$ is accomplished by the formula:

$$V_o = I_u - K \cdot I_c$$

where K is the ratio of the area of the surface 52 to the area of the surface 54. As stated earlier, it is desirable to set these areas equal to each other, where the constant K is equal to one. The amplifier gains $A_1$ and $A_2$ may be set as required to obtain the desired value of K for a particular embodiment of the analyzer 10.

While the above described embodiment of the invention represents a galvanic oxygen analyzer, the invention is by no means limited to such an embodiment. The invention is equally applicable to polarographic analyzers, and analyzers which operate on oxidation reactions as well as reduction reactions, as will be appreciated by those skilled in the art. Many other modifications will occur to those skilled in the art which are within the spirit and scope of the invention. It is thus intended that the invention be limited in scope only by the appended claims.

What is claimed is:

1. In an electrochemical gas sensor for measuring the concentration of a gas in a gas mixture, the sensor including a housing which supports a gas permeable, liquid impermeable membrane, a counter-electrode, a sensing electrode having first and second surfaces, where the first surface is adjacent the membrane, and the second surface is further away from the membrane than the first surface, an electrolyte in contact with the counter-electrode and the first and at least a portion of the second surface of the sensing electrode, and means for enabling the gas to dissolve into the electrolyte, signal means for connecting the sensing and counter electrodes to an electrical circuit to provide a first electrical signal which is related to the concentration of gas dissolved in the electrolyte which contacts the surfaces of the sensing electrode, the improvement comprising:

compensation means for providing a second electrical signal which is related to the concentration of gas dissolved in the electrolyte which contacts the second surface of the sensing electrode, the compensation means including a compensating electrode having a surface substantially coplanar with said at least a portion of the second surface of the sensing electrode and being in contact with the electrolyte, whereby said compensating electrode is positioned for sensing a concentration of the gas to be measured equal to the concentration of the gas at the second surface of the sensing electrode; and means for subtracting the second signal from the first signal to provide a signal which is related to substantially only the concentration of gas dissolved in the thin film of electrolyte which contacts the first surface of the sensing electrode.

2. An electrochemical gas sensor for measuring the concentration of a gas in a gas mixture, comprising:

a housing which supports a membrane which is permeable to the gas;

a counter electrode mounted in the housing;

A sensing electrode mounted within the housing and having first and second surfaces, where the first surface is adjacent the permeable membrane, and the second surface is further away from the permeable membrane than the first surface;

an electrolyte containing within the housing and in contact with the counter electrode and the first surface of the sensing electrode, and a portion of the second surface of the sensing electrode, and into which electrolyte the gas is dissolved as it passed through the permeable membrane;

signal means for connecting the sensing and counter electrodes to an electrical circuit to provide a first electrical signal which is related to the concentration of gas dissolved in the electrolyte which contacts the surfaces of the sensing electrode; and compensation means including a compensating electrode for providing a second electrical signal which is related to the concentration of gas dissolved in the electrolyte which contacts the said portion of the second surface of the sensing electrode, said compensating electrode having a surface substantially coplanar with said portion of the second surface of the sensing electrode.

3. The sensor of claim 2 in which the compensation means includes an electrical insulator which is impermeable to the gas and electrolyte and has first and second opposing surfaces, where the first insulator surface covers all but the mid portion of the second surface of the sensing electrode, whereby the gas dissolved in the electrolyte cannot contact the covered surface, and the compensating electrode covers a predetermined area of the second insulator surface and is in contact with the electrolyte.

4. The sensor of claim 3 further including means for subtracting the second signal from the first signal to provide a signal which is related to only the concentration of gas dissolved in the thin film of electrolyte which contacts the first surface of the sensing electrode.

5. The sensor of claim 3 where the second signal is multiplied by a constant equal to the ratio of the area of the said portion of the second surface of the sensing electrode to the area of the compensating electrode, and the product of the second signal and the constant is subtracted from the first signal to provide a signal which is related to substantially only the concentration of gas dissolved in the thin film of electrolyte which contacts the first surface of the sensing electrode.

* * * * *